(12) United States Patent
Ippoliti et al.

(10) Patent No.: US 8,148,173 B2
(45) Date of Patent: Apr. 3, 2012

(54) POLYMERIZABLE CHEMILUMINESCENT COMPOUNDS

(75) Inventors: Joseph Thomas Ippoliti, Woodbury, MN (US); Joshua Cole Speros, Hayward, WI (US)

(73) Assignee: University of St. Thomas, St. Paul, MN (US)

( * ) Notice: Subject to any disclaimer, the term of this patent is extended or adjusted under 35 U.S.C. 154(b) by 824 days.

(21) Appl. No.: 12/053,992

(22) Filed: Mar. 24, 2008

(65) Prior Publication Data
US 2008/0233601 A1     Sep. 25, 2008

Related U.S. Application Data

(60) Provisional application No. 60/920,067, filed on Mar. 24, 2007.

(51) Int. Cl.
*G01N 33/533*     (2006.01)
*C07D 237/30*     (2006.01)
(52) U.S. Cl. ........................ 436/546; 544/237
(58) Field of Classification Search .................. None
See application file for complete search history.

(56) References Cited

U.S. PATENT DOCUMENTS

| | | | |
|---|---|---|---|
| 2,721,189 | A | 10/1955 | Anderson et al. |
| 3,330,815 | A | 7/1967 | McKeon et al. |
| 7,148,302 | B2 | 12/2006 | Lipian |
| 7,312,285 | B2 | 12/2007 | Chun et al. |

OTHER PUBLICATIONS

Achyuthan, Komandoor E. (1998) "Enzymatic and kinetic properties of blood coagulation factor XIIIa and guinea pig liver transglutaminase utilizing 6-[N-(4-aminobutyl)-N-ethylamino]-2,3-dihydrophthalizine-1,4-dione, as a novel, specific and sensitive chemiluminescent substrate" J. Bioluminescence and Chemiluminescence, 13:1-11.
Hauptmann et al. (2000) "Concepts for the Syntheses of Biotinylated Steroids" Bioconjugate Chem. 11:239-252.
Schnecko et al. (1971) "Copolymers of Ethylene with Bicyclic Dienes" Die Angewandte Makromolekulare Chemie, 20(283):141-152.
Schroeder et al. (1978) Monitoring specific protein-binding reactions with chemiluminescence Methods in Enzymology 57:427-437.

*Primary Examiner* — Shafiqul Haq
(74) *Attorney, Agent, or Firm* — Joseph T. Leone, Esq.; DeWitt Ross & Stevens S.C.

(57) ABSTRACT

Disclosed are compounds having the formula:

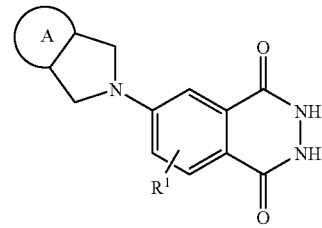

wherein $R^1$ is selected from the group consisting of hydrogen, $C_1$-$C_6$ alkyl, amino, N—$C_1$-$C_6$-alkylamino, and N,N—$C_1$-$C_6$-dialkylamino; and ring "A" is selected from the group consisting of unsubstituted or substituted $C_4$-$C_8$-cycloalkenyl, unsubstituted or substituted bicyclo[2,2,1]alkenyl, and unsubstituted or substituted bicyclo[2,2,2]alkenyl, unsubstituted phenyl, and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl; polymers made from these compounds, and ELISAs that use the compounds and polymers as a chemiluminescent detection label.

18 Claims, 1 Drawing Sheet

"Labeled" Antigens

"Labeled" antigens are attached, free antigens are washed away, and light signal is measured.

Solid Support    Antibodies

Antibodies are attached to a solid support, and free antibodies are washed away.

"Labeled" Antigens

"Labeled" antigens are attached, free antigens are washed away, and light signal is measured.

Antigens

Antigens are added and they replace the "labeled" ones. A new light signal is measured and quantified.

FIG. 1C                                    FIG. 1D

POLYMERIZABLE CHEMILUMINESCENT COMPOUNDS

CROSS-REFERENCE TO RELATED APPLICATIONS

Priority is hereby claimed to provisional application Ser. No. 60/920,067, filed Mar. 24, 2007, which is incorporated herein by reference.

BACKGROUND

Chemiluminescent compounds have become widely used in many biological detection experiments. In fact, uses have ranged from detection of blood coagulation chemicals in guinea pigs to steroid detection in humans. (See Achyuthan, Komandoor E. "Enzymatic and kinetic properties of blood coagulation factor XIIIa and guinea pig liver transglutaminase utilizing 6-[N-(4-aminobutyl)-N-ethylamino]-2,3-dihydrophthalizine-1,4-dione, as a novel, specific and sensitive chemiluminescent substrate." *J. Bioluminescence and Chemiluminescence*, 13. (1998): 1-11, and Luppa, Peter B. "Concepts for the Syntheses of Biotinylated Steroids." *Bioconjugate Chem.*, 11. (2000): 239-252, respectively.) Three common luminescent compounds are luminol (I), isoluminol (II), and diethyl isoluminol (III). These compounds emit light when oxidized by hydrogen peroxide in the presence of iron.

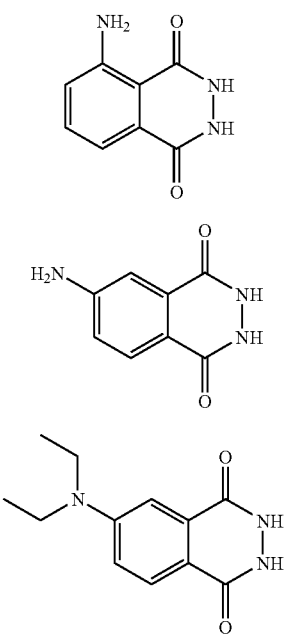

Norbornenes are important monomers in ring-opening metathesis polymerizations (ROMP), using, for example, Grubbs' catalyst:

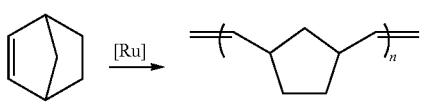

Norbornenes can also be polymerized by other routes, such as addition/vinyl, cationic, and free radical polymerization. See, for example, U.S. Pat. Nos. 7,312,285 and 7,148,302. Note that different polymerization routes will yield polymers having different structures.

SUMMARY OF THE INVENTION

A first version of the invention is directed to a compound comprising a structure of Formula I:

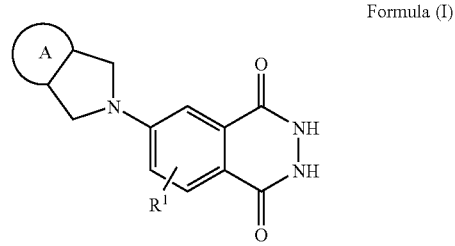

Formula (I)

wherein $R^1$ is selected from the group consisting of hydrogen, $C_1$-$C_6$ alkyl, amino, N—$C_1$-$C_6$-alkylamino, and N,N—$C_1$-$C_6$-dialkylamino; and ring "A" is selected from the group consisting of unsubstituted or substituted $C_4$-$C_8$-cycloalkenyl, unsubstituted or substituted bicyclo[2,2,1]alkenyl, unsubstituted or substituted bicyclo[2,2,2]alkenyl, unsubstituted phenyl, and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl.

The preferred compounds according to the first version of the invention comprise a structure of Formula I:

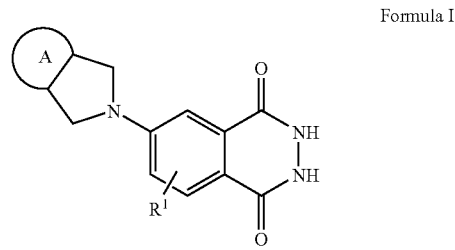

Formula I wherein $R^1$ is hydrogen; and ring "A" is selected from the group consisting of unsubstituted or substituted $C_4$-$C_8$-cycloalkenyl, unsubstituted or substituted bicyclo[2,2,1]alkenyl, unsubstituted or substituted bicyclo[2,2,2]alkenyl, and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl.

The most preferred compounds of the first version of the invention are:

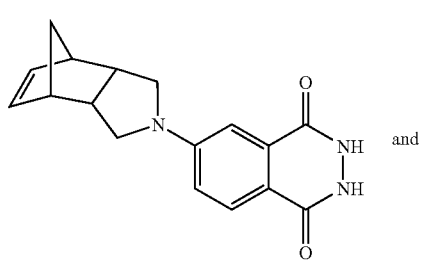

and

A second version of the invention is a polymer produced by polymerizing or co-polymerizing compounds having a structure as shown in Formula I. The polymerization may be accomplished by any means now known in the art or developed in the future for polymerizing compounds having a reactive ethylene moiety. The preferred polymers are made by a ring-opening metathesis reaction. Homopolymers of a Formula I compound are preferred. Copolymers of Formula I compounds, as well as co-polymers of Formula I compounds and other monomers are also within the scope of the present invention.

A third version of the invention is directed to an enzyme-linked immunosorbent assay in which a compound as shown in Formula I is used as a chemiluminescent detection label. In another embodiment of this third version of the invention, a polymer comprising monomers which are the Formula I compounds is used as the chemiluminescent detection label.

BRIEF DESCRIPTION OF THE DRAWINGS

FIGS. 1A, 1B, 1C, and 1D together schematically depict a competitive enzyme-linked immunosorbent assays (ELISA). FIG. 1A depicts capture antibodies linked to a solid support. FIG. 1B depicts chemiluminescent-labeled antigens being reversibly attached to the capture antibodies. The compounds and polymers of the present invention are useful as the chemiluminescent label. A first light signal is measured at this point. FIG. 1C depicts a known amount of a second, unlabeled antigen (distinct from the first antigen) competing for binding sites occupied by chemiluminescent-labeled first antigens. FIG. 1D depicts the support after the competitive binding. A second light signal is measured at this point. The amount or activity of the first labeled antigen can be determined by the difference between the two light signals. (See Crowther, John R. "The ELISA Guidebook," Totowa, N.J.: Humana Press, 2001)

DETAILED DESCRIPTION

The invention is directed to novel chemiluminescent compounds and polymers formed from the compounds. The compounds and polymers that incorporate the compounds are highly chemiluminescent and are thus useful as detection labels in chemiluminescent assays in general and enzyme-linked immunosorbent assays (ELISA) in particular. The compounds comprise a luminescent moiety, preferably luminol or a luminol derivative, and a polymerizable, fused-ring moiety comprising a pyrrolidinyl group fused to a group that contains a polymerizable ethylene group, such as a alkenyl-, acyl-, or acrylamido-substituted phenyl, a substituted or unsubstituted norbornene, a substituted or unsubstituted bicyclo-octene, and the like. The compounds are polymerizable by several different routes and the resulting polymers can likewise be used as chemiluminescent labels in any assay where such labels are used.

Figure 1A:
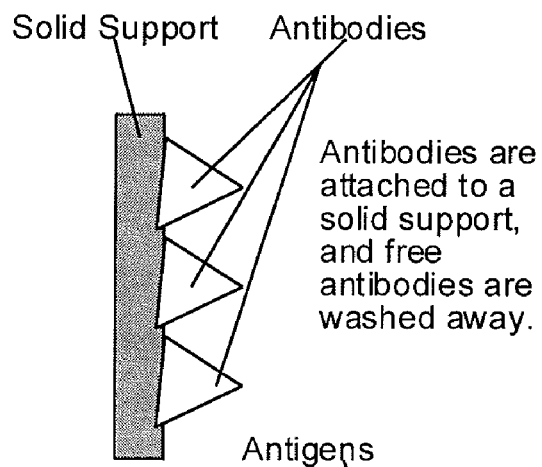
Figure 1B:
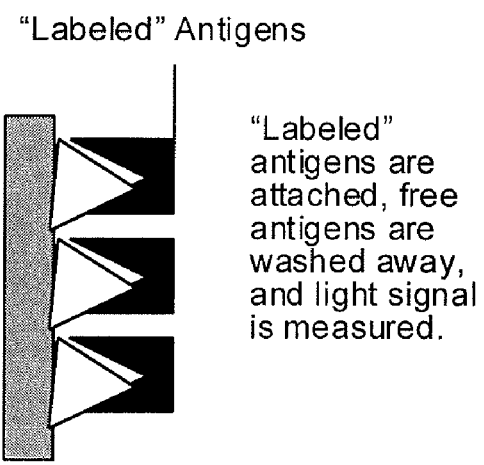
Figure 1B:
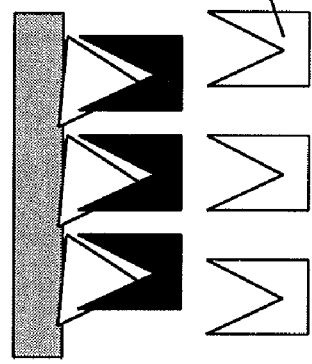
Figure 1B:
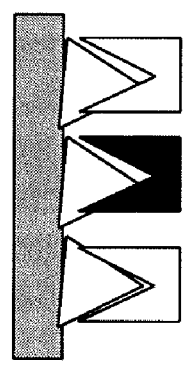

The primary advantage and utility of the novel compounds and polymers disclosed herein are chemiluminescent. Thus, they can be used in any application where a chemiluminescent compound is needed. The primary utility of the compounds is for use as detection reagents in ELISAs. ELISAs involve attaching a capture antibody to a solid support. One of the many types of ELISAs is shown schematically in FIG. 1A. (Many other formats are known; see Crowther, "The ELISA Guidebook," supra.) Any free antibodies are washed off the support. (If required, any exposed surfaces of the support are blocked with a non-specific reagent such as bovine serum albumin.). Antigens with a luminescent moiety are then exposed to the treated surface. The immobilized antibodies capture the labeled antigen. The compounds and polymers of the present invention are used as the luminescent moiety. This is shown schematically in FIG. 1B. The resulting labeled antigens are referred to simply as "labeled." The light intensity signals from these labeled antigens provide a means of determining the presence and/or concentration and/or activity of an analyte in a sample by comparing the signal generated by the sample to a standard curve. In a competitive ELISA, the signal from the sample is first taken. This first signal would thus be taken at the point in the assay shown in FIG. 1B.

Then a known amount of additional analyte is added. This step is depicted schematically in FIG. 1C. The added analyte competes with the antigens already captured by the immobilized antibodies and displaces some or all of the labeled antigens due to their greater affinity for the antibody. As a result, a lowered light intensity is measured. This step is depicted in FIG. 1D. The displacement of some of the labeled antigens (which contributed to the first light measurement) allows for a calculation of the amount of analyte that is present in the sample by difference between the first light measurement and the second.

Making the Monomers:

The new luminol derivatives according to the present invention have a two-fold advantage over conventional means of luminescent detection. First, the compounds comprise a polymerizable component, which increases both sensitivity and detection capabilities. Increased sensitivity results from the luminescence of many derivatives per analyte molecule. The detection capabilities are also heightened as a result of the increased intensity as the concentration of analyte increases. Additionally, due to its planar, electron-donating five-membered ring component, compound 7 yields a more intense luminescence as compared to other luminescent compounds. See, for example, Schroeder et al. (1978) "Monitoring specific protein-binding reactions with chemiluminescence," *Methods in Enzymology* 57:427-437.

Reaction Scheme 1: Synthetic Route for Fabricating the Preferred Compound

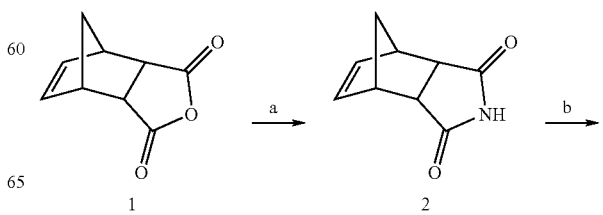

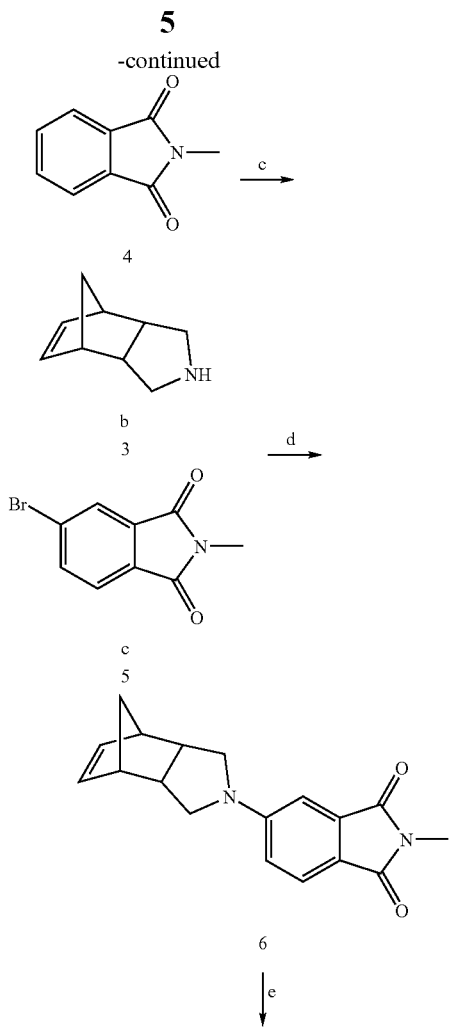

a = NH$_3$(aq.)
b = LAH, THF
c = KBrO$_3$, H$_2$SO$_4$
d = Pd Catalyst, DME
e = NH$_2$NH$_2$ The preferred synthetic route to the preferred compound of Formula I is depicted in Reaction Scheme 1. The initial synthetic step can be accomplished one of two ways. The first route involves cracking dicyclopentadiene and performing a Diels-Alder reaction with the resulting cyclopentadiene and maleimide. This route yields a mixture of endo and exo products. The second route involves refluxing the cis-5-norbornene-endo-2,3-dicarboxylic anhydride with toluene and urea. This second route functions, but is not preferred because it proceeds in poor yields.

The preferred synthetic route, which is novel and is encompassed by the present invention utilizes a microwave synthesizer, for example, a "BIOTAGE INITIATOR"-brand microwave synthesizer. In this route, in step (a) of Reaction Scheme 1, the corresponding anhydride 1 was reacted with ammonium hydroxide for 5 minutes at 150° C. This yields either endo or exo products 2 depending on the starting material. This first step yields pure product with minimal workup in acceptable yield (average of 56%). This new methodology also saves time, materials, and energy.

Step (b) of Reaction Scheme 1 is a LiAlH$_4$ reduction to yield 4. This step also proceeds in high yield. Step (c) of Reaction Scheme 1 requires forming a brominated N-methylphthalimide 5. This is accomplished by stirring the imide 4 with potassium bromate in sulfuric acid at room temperature for 3-4 hours. This step proceeded in good yield because hydrobromous acid (HOBr) is created in situ and proved to be an excellent brominating agent for the deactivated aromatic ring of the N-methylphthalimide 4. Compounds 3 and 5 are then reacted together in step (d) to yield compound 6. This step is accomplished via a palladium-catalyzed Buchwald-Hartwig coupling to yield 6. (See the Examples for further details of the coupling.) Reaction of 6 with hydrazine (analogous to Einhom-Brunner reaction) yields the target compound 7 in high yield.

Compound 7 can then be polymerized in the same fashion as conventional norbornene-containing compounds. Thus, compound 7 can be polymerized via ring-opening metathesis reaction, vinyl addition polymerization, and the like.

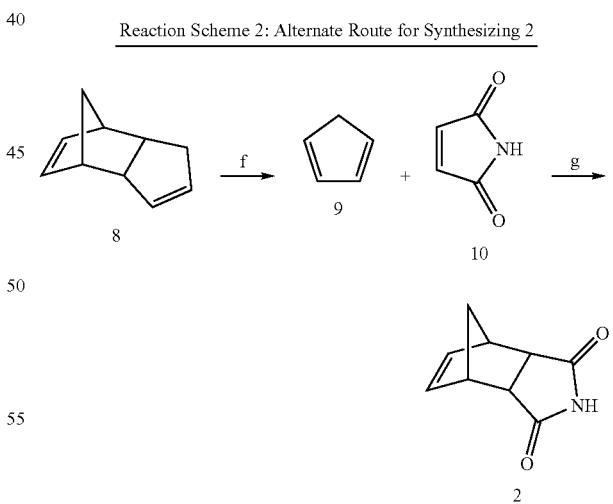

Reaction Scheme 2: Alternate Route for Synthesizing 2 f = crack (230° C.)
g = Diels-Alder (room temp.)

An alternative route to compound 2 is shown in Reaction Scheme 2. Here, dicyclopentadiene 8 is cracked into cyclopentadiene 9. The cyclopentadiene 9 is then reacted with maleimide 10 to yield the desired intermediate 2.

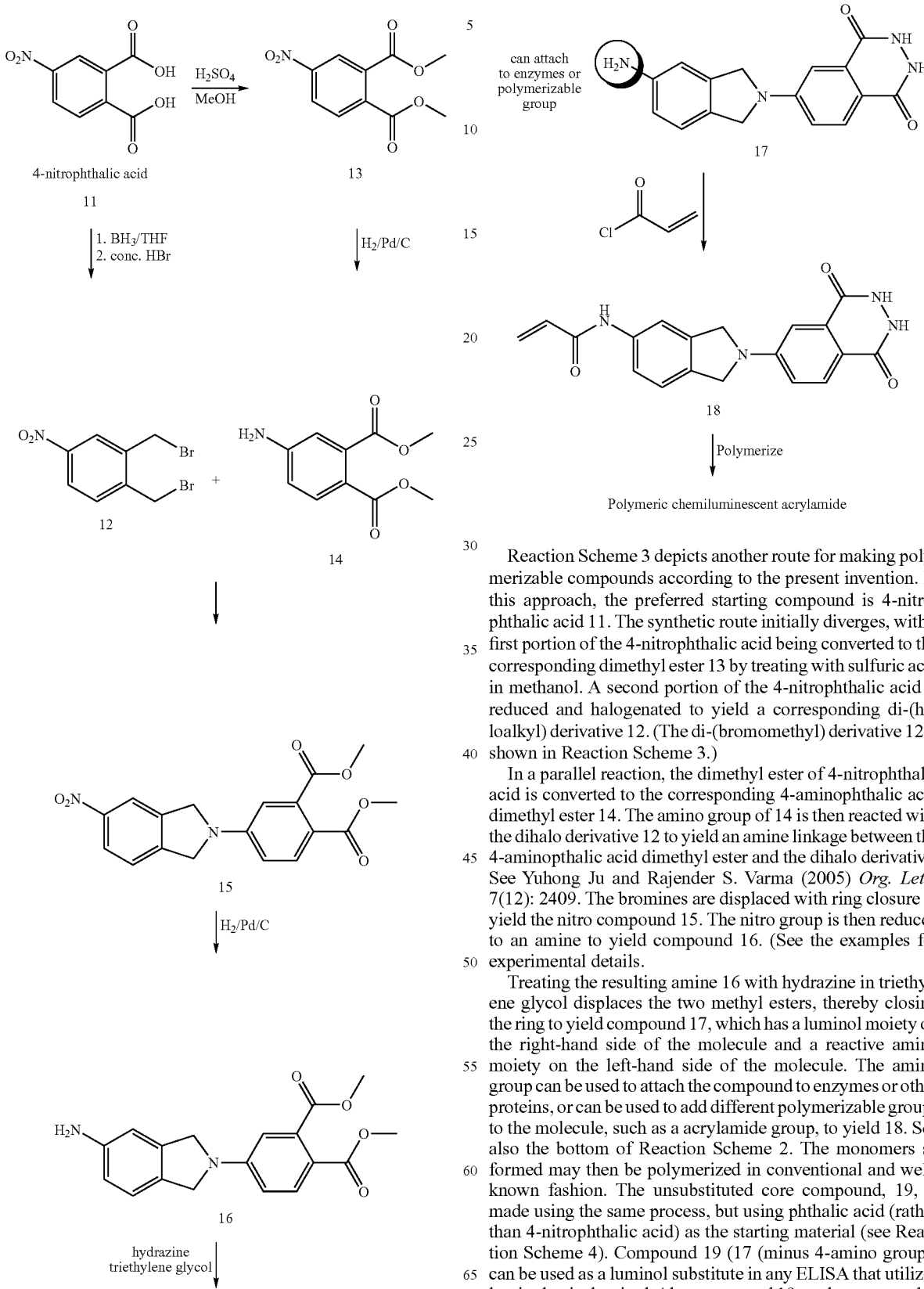

Reaction Scheme 3 depicts another route for making polymerizable compounds according to the present invention. In this approach, the preferred starting compound is 4-nitrophthalic acid 11. The synthetic route initially diverges, with a first portion of the 4-nitrophthalic acid being converted to the corresponding dimethyl ester 13 by treating with sulfuric acid in methanol. A second portion of the 4-nitrophthalic acid is reduced and halogenated to yield a corresponding di-(haloalkyl) derivative 12. (The di-(bromomethyl) derivative 12 is shown in Reaction Scheme 3.)

In a parallel reaction, the dimethyl ester of 4-nitrophthalic acid is converted to the corresponding 4-aminophthalic acid dimethyl ester 14. The amino group of 14 is then reacted with the dihalo derivative 12 to yield an amine linkage between the 4-aminopthalic acid dimethyl ester and the dihalo derivative. See Yuhong Ju and Rajender S. Varma (2005) *Org. Lett.*, 7(12): 2409. The bromines are displaced with ring closure to yield the nitro compound 15. The nitro group is then reduced to an amine to yield compound 16. (See the examples for experimental details.

Treating the resulting amine 16 with hydrazine in triethylene glycol displaces the two methyl esters, thereby closing the ring to yield compound 17, which has a luminol moiety on the right-hand side of the molecule and a reactive amino moiety on the left-hand side of the molecule. The amino group can be used to attach the compound to enzymes or other proteins, or can be used to add different polymerizable groups to the molecule, such as a acrylamide group, to yield 18. See also the bottom of Reaction Scheme 2. The monomers so formed may then be polymerized in conventional and well-known fashion. The unsubstituted core compound, 19, is made using the same process, but using phthalic acid (rather than 4-nitrophthalic acid) as the starting material (see Reaction Scheme 4). Compound 19 (17 (minus 4-amino group)) can be used as a luminol substitute in any ELISA that utilizes luminol or isoluminol. Also compound 19 can be converted to other derivatives as illustrated in Scheme 4.

Reaction Scheme 4

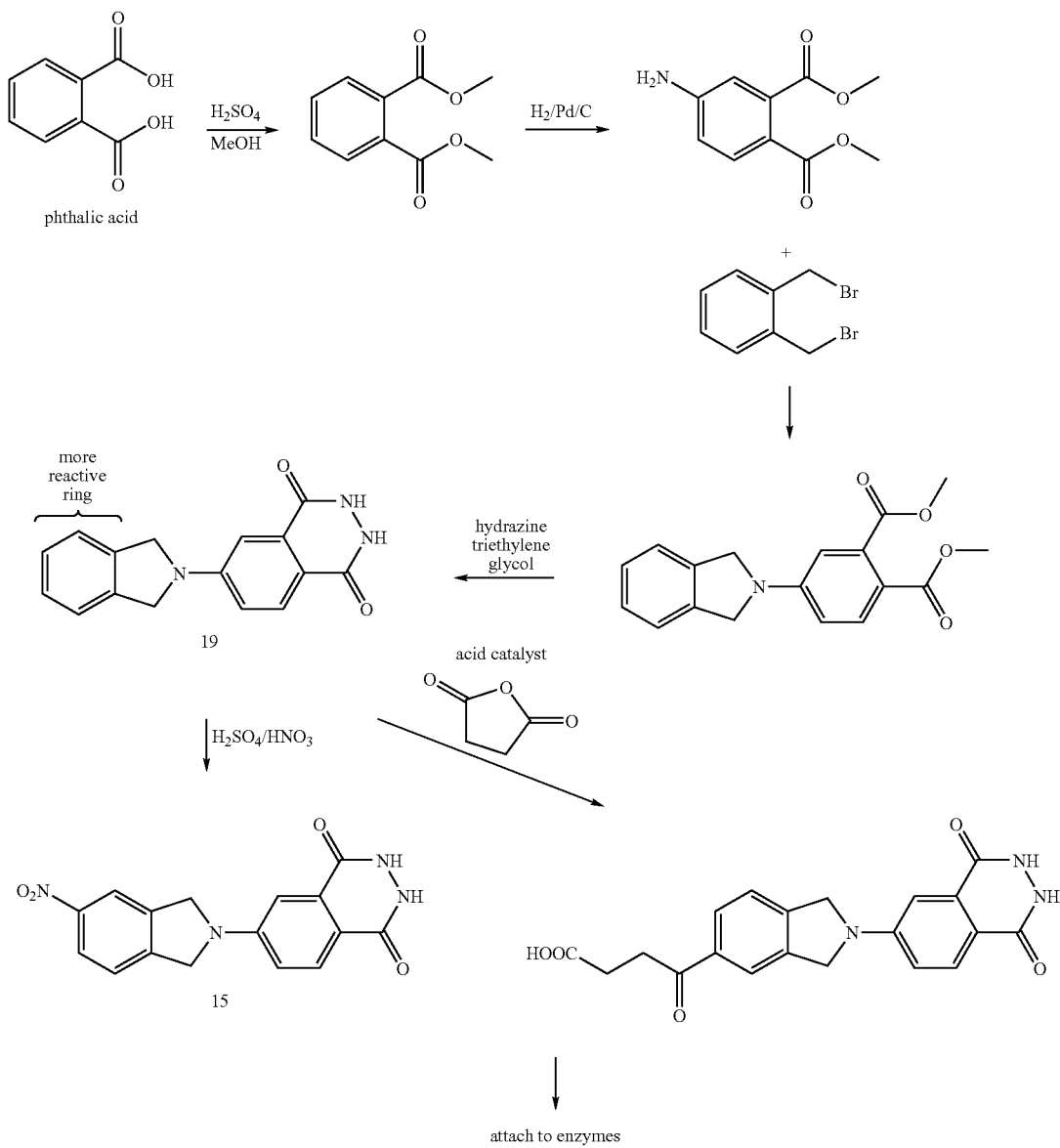

Making the Polymers:

For compounds disclosed herein that include a bicycloalkenyl moiety, the polymers according to the present invention may be made by any means now known or developed in the future for polymerizing bicycloalkenes, including ring-opening polymerization, addition polymerization, vinyl polymerization, ethylene-bicycloalkene co-polymerization, and radical or cationic polymerization. Note that these routes yield different types of polymers. For purposes of brevity only, the following discussion will refer to norbornene as the moiety that undergoes polymerization. This is for brevity only. The norbornene moiety serves as a representative example for the polymerization of bicycloalkenyl groups in general.

The general polymerization mechanisms and their resulting polymerization products are as follows:

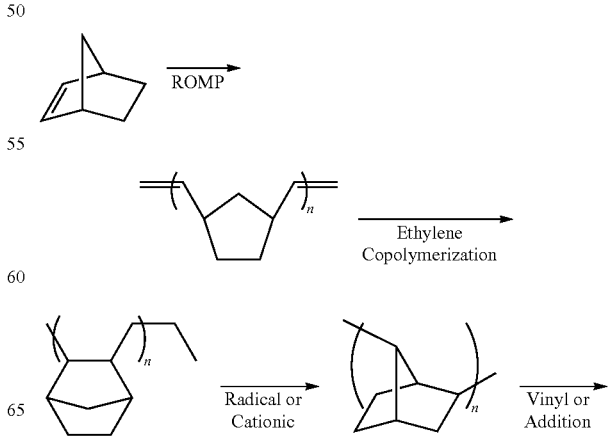

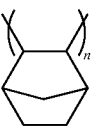

An early synthesis of polynorbornene (poly(bicyclo[2.2.1]hept-2-ene), hereinafter poly-NB) is disclosed in U.S. Pat. No. 2,721,189, issued Oct. 18, 1955, incorporated herein by reference. The polymer resulting from this approach was found to contain two types of polymers, one brittle, the other thermoformable. The brittle polymer was found to be a low molecular-weight saturated polymer which was an addition type polymer. The thermoformable polymer was shown to be formed by a ring-opening metathesis polymerization (ROMP). The ROMP mechanism yields a different structure as compared to addition polymerization mechanism in two important details: the ROMP mechanism yields a repeat unit with one less cyclic unit than the starting monomer; and (ii) the polymer backbone includes double bonds. Both mechanisms and the resulting polymers are within the scope of the present invention. The two types of polymers appear as follows (again using norbornene as the model moiety being polymerized:

ROMP Mechanism Product:

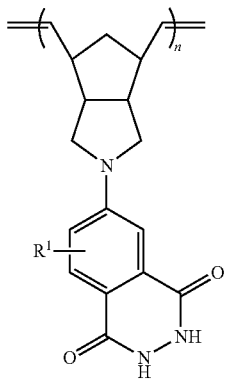

Addition Polymerization Mechanism Product:

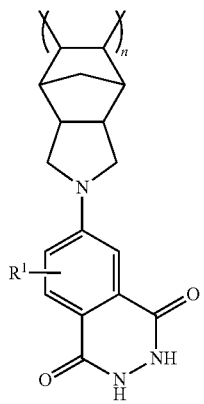

Since the issuance of U.S. Pat. No. 2,721,189 in 1955, reaction conditions have been optimized so as to enable selective synthesis of either the addition polymer, or the ROMP polymer. For instance, U.S. Pat. No. 3,330,815 describes a method for selectively making the addition polymer using aTiCl$_4$/Et$_2$AlCl or a Pd(C$_6$H$_5$CN)$_2$Cl$_2$, catalyst. The method described in this patent may be used to polymerize the bicycloalkene-containing compounds described herein. The addition polymers produced by this route have a molecular weight range from about 500 to about 750 Da.

Allylnickelhalides have also been used to produce poly-NBs. The molecular weights of the polymers produced by this route are from about 1000 to about 1500 Da. See Porri et al. (1964). *Gallazzi Chim. Ind. (Milan)*, 46:428. Addition polymers of the compounds disclosed herein can also be produced using zirconocene-type catalysts such as those described by Kaminsky et al. (1992) *J. Mol. Cat.* 74: 109, incorporated herein The molecular weight of the resulting polymer can be controlled by (i) varying the amount of the transition metal catalyst used; (ii) varying the polymerization temperature; and/or (iii) using hydrogen as a chain transfer agent. See, for example, EP 445,755A and Schnecko et al. (1971) "Copolymers of Ethylene with Bicyclic Dienes" *Die Angewandte Makromolekulare Chemie,* 20(283):141-152.

As a general rule, Zr-, Ni-, and Pd-containing catalysts are preferred for vinyl-addition polymerization. while Mo-, W-, Re-, and Ru-containing catalysts are preferred for ROMP. Techniques for ROMP of bicycloalkenes are widely known in the art and will not be described herein. An exhaustive treatment of the subject can be found in "Ring-Opening Metathesis Polymerization and Related Chemistry," Ezat Khosravi & Teresa Szymanska-Buzar, Eds., © 2002, Kluwer Academic Publishers, ISBN 1-4020-0558-X.

Acryl-containing and acrylamide-containing monomers of Formula I may also be polymerized in conventional fashion. Acrylamide-containing monomers are preferably polymerized via free-radical polymerization using any suitable initiator, such as a combination of ammonium persulfate and tetramethyl ethylene diamine (TEMED). Other initiators are well-known to those skilled in the art and may be used in the present invention.

EXPERIMENTAL

The following Examples are included solely to provide a more complete description of the invention disclosed and claimed herein. The Examples do not limit the scope of the invention described or claimed herein in any fashion.

Example 1

Microwave Synthesis of Imide 2 from Either Endo or Exo Isomer of 1

The cis-5-norbornene-endo/exo-2,3-dicarboxylic anhydride was run in a "BIOTAGE INITIATOR"-brand microwave synthesizer with aqueous ammonium hydroxide. The method resulting in highest yield (64.5%) involved adding 1.0290 g of the anhydride to 1.5 mL of aqueous ammonium hydroxide (14.8 M). A stirring bar was added and the 0.5-2.0 mL microwave vial was capped. The microwave was run at 5 minutes at 150° C. with the absorbance set at very high. Workup involved allowing the crystals to crash out of solution and filtering, by suction, through a size D frit. The crystals were washed twice with 10 mL of cold water.

Example 2

Diels-Alder Reaction of Cracked Dicyclopentadiene 8 with Malimide 10

The second method of creating the imide involved two steps. The first step was to crack about 44.0 mL of dicyclopentadiene into 34.7 mL of cyclopentadiene. This was done by adding the dicyclopentadiene drop-wise through a liquid addition funnel to silicone oil held at about 230° C. The resulting cyclopentadiene was captured using a distillation apparatus. The round bottom flask containing the cyclopentadiene was immediately capped and placed in the refrigerator. A room temperature Diels-Alder reaction was performed by adding 2.495 g of cyclopentadiene to 3.6648 g of maleimide into 10 mL of tetrahydrofuran (THF). This was allowed to stir in a 100 mL round-bottom flask for about an hour. The resulting product was filtered through a size D frit by suction. It was washed with hexanes and distilled water. This reaction was performed in about 83% yield.

Example 3

Lithium Aluminum Hydride Reduction of Imide 2 to Amine 3

To a 250 mL two-neck round-bottom flask a stir bar and 50 mL of anhydrous THF were added. Then 1.4185 g of LAH was added to this flask. The flask was sealed with a glass stopper on one neck and on the other a reflux condenser. The reflux apparatus was put under a nitrogen purge. 2.0059 g of the starting imide was dissolved in anhydrous THF and injected into the round bottom. The Variac heater was set at about 40 and the round-bottom was left to reflux for 3 hours. After reflux the flask was removed from heat, and 2 mL of water were slowly added followed by the slow addition of 2 mL of a 10% sodium hydroxide solution. Then 3 mL of water were added. This resulted in the formation of a white lithium aluminum hydroxide salt. The solution was filtered through a pad of celite on a size D frit and washed with cold ether. The filtrate was dried with sodium bicarbonate. Again it was filtered through a size D frit and washed with cold ether. Rotovapped the filtrate and put the resulting brown oil on vacuum overnight. A tan solid was left and H-NMR showed this to be the desired amine. The yield this reaction was performed with was 78%.

Example 4

Monobromination of N-Methylphthalimide 4 Using Potassium Bromate and Sulfuric Acid The monobromination involved adding 50 mL of water to a 250 mL round-bottom flask. Then 50 mL of 18.0 M sulfuric acid were slowly added. The flask was kept on an ice bath and stirred to keep the solution cool. Then 3.0026 g of N-methylphthalimide were added to the solution and allowed to stir for five minutes. Then 3.4729 g of potassium bromate were added. The solution turned light orange and was allowed to stir at room temperature for five hours. The orange solution was then poured into 300 mL of cold water. A few spatulas full of sodium bisulfite were added to remove the bromine. The solution changed from a pale orange to off-white. The solution was filtered by suction on a size D frit and washed twice with 50 mL of cold water. The solid sat on suction for 20 minutes to aid in drying. H-NMR showed that the 2.9877 g (67% yield) of product was pure monobrominated N-methylphthalimide.

Example 5

Buchwald-Hartwig Palladium Catalyzed Coupling of Monobrominated N-Methylphthalimide 5 and Amine 3

Here, a 100 mL round-bottom flask with a stirbar is flame dried. To this flask 0.5209 g of the amine and 0.9249 g of the monobrominated substrate were added. The flask was then capped with a rubber septum and put under a nitrogen purge. Then 25 mL of anhydrous 1,2-dimethoxyethane (DME) were canulated into the flask.

To a separate flame-dried 100 mL round-bottom flask 0.1336 g of [1,3-bis(2,6-diisopropylphenyl)-imidazol-2-ylidene](3-chloropyridyl)-palladium (II) dichloride ("PEPPSI") and 0.6487 g of potassium tert-butoxide were added in a nitrogen glovebox. 5 mL of anhydrous DME was canulated through the septum into the flask.

The first flask was allowed to stir until the solids dissolved. The solution was then injected into the second flask containing the potassium tert-butoxide and PEPPSI. The solution went from pale yellow to light pink in color. The round bottom flask was allowed to stir for 2 hours in an oil bath held at 50° C. Then it was allowed to stir overnight at room temperature. The light pink solid was filtered through a size M frit by suction. The solid was dissolved in water and extracted with dichloromethane. The dichloromethane extract was rotovapped and an H-NMR was taken of the resulting brown solid, which contains the target compound in low yield.

Example 6

Compound 11 to Compound 13 (see Reaction Scheme 3)

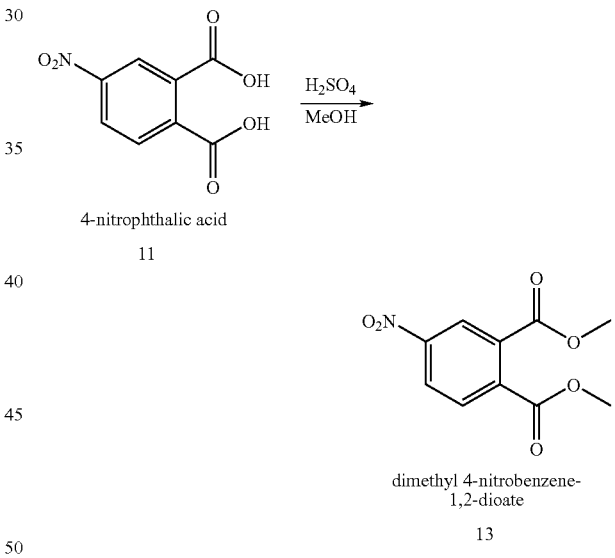

To a 500 mL round-bottom flask was added a stirbar, nitrophthalic acid (4.54 g, 21.5 mmol), ~200 mL of anhydrous methanol, and 5 drops of conc. sulfuric acid (catalyst). The round-bottom was fitted with a reflux condenser and refluxed for about a week under $N_2$ with a cooling water line. It is very important that the methanol be dry because the reaction is an equilibrium that needs to be driven to the right. After reflux, the crude reaction mixture was spotted on TLC (50:50, hexanes:ethyl acetate). The reaction is complete when TLC shows only one spot (which is the product). If a faint second spot is present, the reaction needs to be run longer; this second spot is starting material. After TLC confirmed product, the cooled reaction mixture was poured into ~600 mL of ice cold 5% $NaHCO_3$ solution. An off-white solid precipitated. The precipitate was filtered by suction through a fritted funnel, rinsed with 300 mL of cold 5% $NaHCO_3$ solution, dried on suction for about 30 min., and placed in vacuum oven (~50° C.) overnight. ¹H-NMR: 6H singlet, ẟ4.0; 1H doublet, ẟ7.9; 1H doublet, ẟ8.45; 1H singlet ẟ8.65).

Example 7

Compound 13 to Compound 14 (see Reaction Scheme 3)

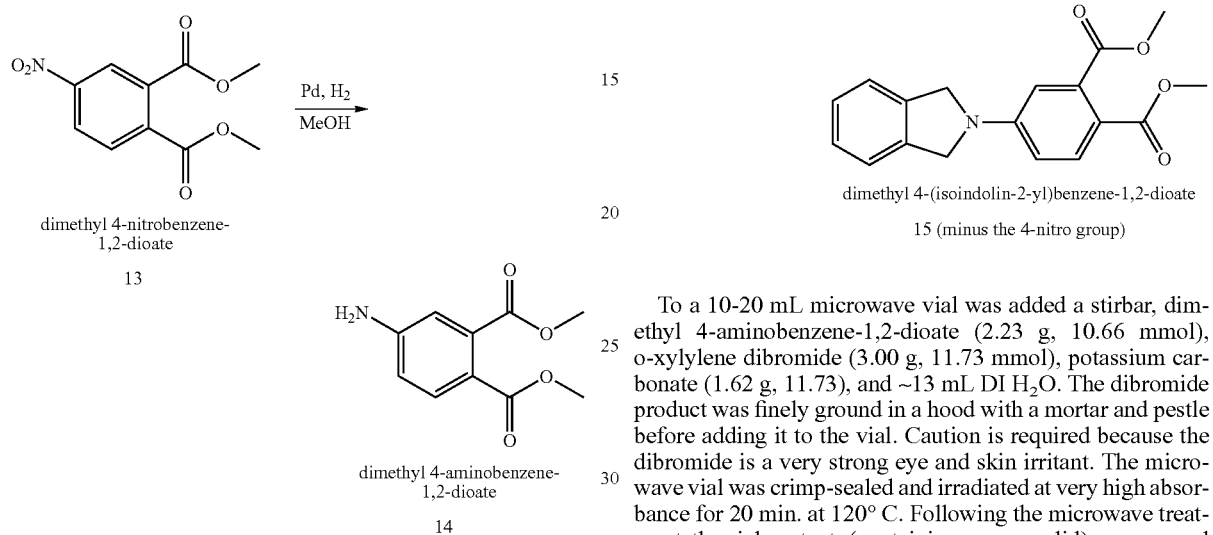

To a flame-dried 500 mL round-bottom flask was added a stirbar, dimethyl 4-nitrobenzene-1,2-dioate (4.00 g, 16.7 mmol), and ~300 mL anhydrous methanol. The mixture was stirred until all solids dissolved. Very slowly was added 10% palladium on carbon (800 mg, ~5 mol %). The palladium on carbon can flash and cause fire or a small explosion, so great care must be taken to add the palladium/C slowly. Following addition of palladium on carbon, the round-bottom flask was capped and purged with $N_2$ for ~5 min. The round-bottom flask was then purged with $H_2$ briefly before leaving under positive $H_2$ pressure. The flask was then stirred overnight at room temperature. The reaction mixture was filtered by suction through a pad of celite on a fritted funnel, and then thoroughly rinsed with methanol. Rotary evaporation yielded an off-white solid, which was dried overnight in a vacuum oven (~50° C.). Purity was checked via TLC. The TLC plate was stained with ninhydrin and placed on hot plate; the product generated a bright pink spot. ¹H-NMR: 3H singlet, ẟ3.84; 3H singlet, ẟ3.90; 2H broad singlet, ẟ4.13; 2H multiplet, ẟ6.70; 1H doublet, ẟ7.725).

Example 8

Compound 15 and Derivative Thereof (see Reaction Scheme 3)

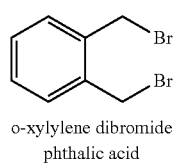

o-xylylene dibromide
phthalic acid

+

To a 10-20 mL microwave vial was added a stirbar, dimethyl 4-aminobenzene-1,2-dioate (2.23 g, 10.66 mmol), o-xylylene dibromide (3.00 g, 11.73 mmol), potassium carbonate (1.62 g, 11.73), and ~13 mL DI $H_2O$. The dibromide product was finely ground in a hood with a mortar and pestle before adding it to the vial. Caution is required because the dibromide is a very strong eye and skin irritant. The microwave vial was crimp-sealed and irradiated at very high absorbance for 20 min. at 120° C. Following the microwave treatment, the vial contents (containing a green solid) were poured into ~200 mL DI $H_2O$ and stirred for ~20 min., filtering by suction on a fritted funnel, and rinsed generously with DI $H_2O$. The remaining solid was placed into ~100 mL of petroleum ether and stirred for ~5 min. before filtering on the fritted funnel and rinsed with additional petroleum ether, 3×. The solid was then dissolved into ~100 mL of dichloromethane and dripped evenly onto a pad of silica gel (2 in. thick) on a fritted funnel and allowed to dry. The silica gel was then washed with ~300 mL of hexanes followed by 100 mL of 90:10 (hexanes:ethyl acetate). The filtrate, which contains unreacted dibromide, is discarded. The silica gel was washed with 250 mL ethyl acetate and ~250 mL dichloromethane. The fractions were combined and the filtrates rotary evaporated to yield a light brown solid (product). The silica gel was then be flushed with ~300-400 mL of methanol to remove remaining product (which was also collected via rotary evaporation). ¹H-NMR: 3H singlet, ẟ3.85; 3H singlet, ẟ3.95; 4H singlet, ẟ4.70; 2H multiplet, a 6.65; 4H singlet, ẟ7.35; 1H doublet, a 7.875).

Example 9

Compound 17 and Derivatives (Ring Closure to Yield Luminol Moiety)

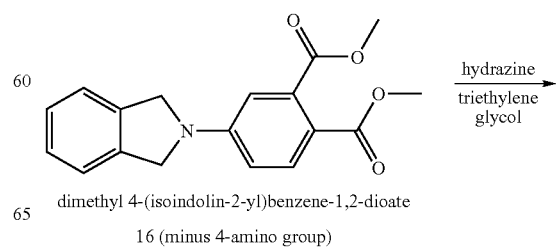

dimethyl 4-(isoindolin-2-yl)benzene-1,2-dioate 16 (minus 4-amino group)

-continued

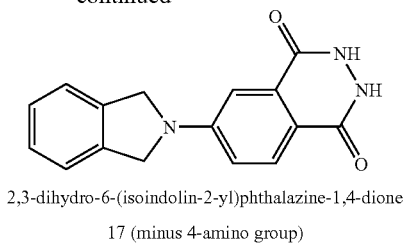

2,3-dihydro-6-(isoindolin-2-yl)phthalazine-1,4-dione 17 (minus 4-amino group)

To a 2-5 mL microwave vial was added a stirbar, dimethyl 4-(isoindolin-2-yl)benzene-1,2-dioate (300 mg, 0.963 mmol), hydrazine (1.21 mL, 25.04 mmol), and triethylene glycol (2.42 mL). The vial was crimp-sealed and irradiated in the microwave at very high absorbance for 7.5 min. at 150° C. After irradiation, the vial was cooled on ice for ~15 min. The reaction mixture was then diluted with ~15 mL DI $H_2O$ and neutralized with dilute (1-3 M) HCl. The product was then filtered by suction on a fritted funnel, and rinsed with copious amounts of DI $H_2O$. A light yellow solid resulted. The light yellow solid was scraped into ~200 mL chloroform and stirred for about 30 min. The reaction solution was filtered through a fritted funnel, dried over suction for ~20 min., and then dried in a vacuum oven (~50° C.) for 2 h. $^1$H-NMR: 4H singlet, ∂4.75; 1H singlet, ∂7.05; 1H doublet, ∂7.20; 2H split singlet, ∂7.35; 2H split singlet, ∂7.45; 1H doublet, ∂7.95).

The purity of the product can be confirmed by performing the "luminol reaction" with the product: About 5 mg of product is stirred into ~20 mL of 50% NaOH. Dilute this solution to 100 mL with DI $H_2O$ ("Solution A"). Prepare "Solution B" by mixing 10 mL 3% $K_3Fe(CN)_6$, 10 mL 3% $H_2O_2$, and 80 mL DI $H_2O$. Dilute about 25 mL of Solution A to 100 mL with DI $H_2O$, Solution A and Solution B are then poured simultaneously into a large Erlemneyer flask in a dark room. A bright turquoise light will result, which then fades to light blue. If dried hemoglobin is added to the flask the light blue light color will persist much longer.

The invention claimed is:

1. A compound having a structure as shown in Formula I:

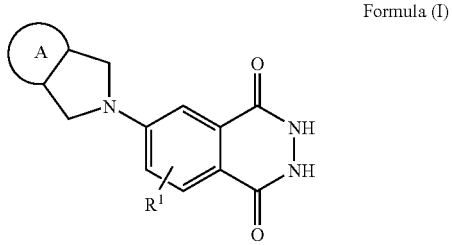

Formula (I)

wherein $R^1$ is selected from the group consisting of hydrogen, $C_1$-$C_6$ alkyl, amino, N—$C_1$-$C_6$-alkylamino, and N,N—$C_1$-$C_6$-dialkylamino; and ring "A" is selected from the group consisting of unsubstituted or substituted $C_4$-$C_8$-cycloalkenyl, unsubstituted or substituted bicyclo[2,2,1]alkenyl, and unsubstituted or substituted bicyclo[2,2,2]alkenyl, unsubstituted phenyl, and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl.

2. The compound of claim 1, wherein $R^1$ is hydrogen.

3. The compound of claim 1, wherein $R^1$ is $C_1$-$C_6$ alkyl.

4. The compound of claim 1, wherein $R^1$ is amino.

5. The compound of claim 1, wherein $R^1$ is N—$C_1$-$C_6$-alkylamino.

6. The compound of claim 1, wherein $R^1$ is N,N—$C_1$-$C_6$-dialkylamino.

7. The compound of claim 1, wherein ring "A" is selected from the group consisting of unsubstituted or substituted $C_4$-$C_8$-cycloalkenyl.

8. The compound of claim 1, wherein ring "A" is selected from the group consisting of unsubstituted or substituted bicyclo[2,2,1]alkenyl.

9. The compound of claim 1, wherein ring "A" is selected from the group consisting of unsubstituted or substituted bicyclo[2,2,2]alkenyl.

10. The compound of claim 1, wherein ring "A" is selected from the group consisting of unsubstituted phenyl, and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl.

11. A compound having a structure as shown in Formula I:

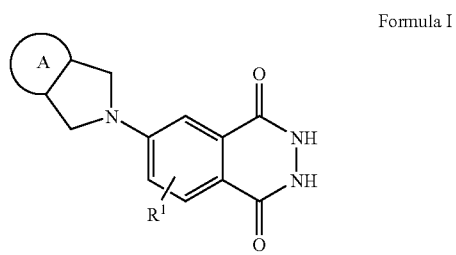

Formula I wherein $R^1$ is hydrogen; and ring "A" is selected from the group consisting of unsubstituted or substituted $C_4$-$C_8$-cycloalkenyl, unsubstituted or substituted bicyclo[2,2,1]alkenyl, and unsubstituted or substituted bicyclo[2,2,2]alkenyl, unsubstituted phenyl, and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl.

12. The compound of claim 11, wherein ring "A" is selected from the group consisting of unsubstituted or substituted $C_4$-$C_8$-cycloalkenyl.

13. The compound of claim 11, wherein ring "A" is selected from the group consisting of unsubstituted or substituted bicyclo[2,2,1]alkenyl.

14. The compound of claim 11, wherein ring "A" is selected from the group consisting of unsubstituted or substituted bicyclo[2,2,2]alkenyl.

15. The compound of claim 11, wherein ring "A" is selected from the group consisting of unsubstituted phenyl and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl.

16. A compound which is:

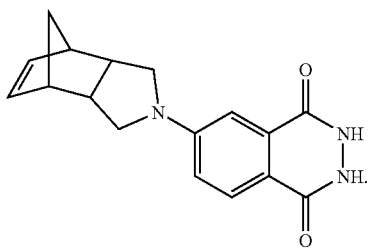

17. A compound which is

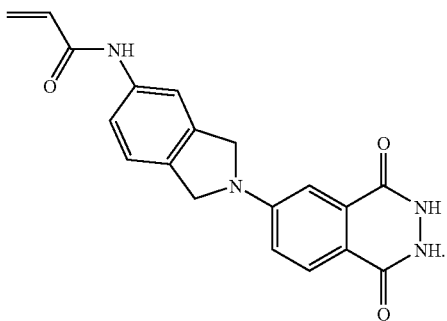

18. A polymer produced by polymerizing a compound a structure of Formula I:

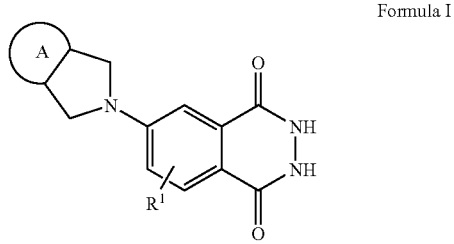

Formula I wherein $R^1$ is selected from the group consisting of hydrogen, $C_1$-$C_6$ alkyl, amino, N—$C_1$-$C_6$-alkylamino, and N,N—$C_1$-$C_6$-dialkylamino; and ring "A" is selected from the group consisting of unsubstituted or substituted $C_4$-$C_8$-cycloalkenyl, unsubstituted or substituted bicyclo[2,2,1]alkenyl, and unsubstituted or substituted bicyclo[2,2,2]alkenyl, unsubstituted phenyl, and phenyl substituted with a moiety selected from the group consisting of $C_3$-$C_6$-alkenyl, acryl, acryl-$C_1$-$C_6$ alkyl, acrylamido, and acrylamido-$C_1$-$C_6$ alkyl.

* * * * *